United States Patent
Kobayashi

(10) Patent No.: US 6,878,674 B2
(45) Date of Patent: Apr. 12, 2005

(54) PESTICIDAL EMULSIFIABLE CONCENTRATE COMPOSITION

(75) Inventor: Mamoru Kobayashi, Funabashi (JP)

(73) Assignee: Nissan Chemical Industries, Ltd., Tokyo (JP)

(*) Notice: Subject to any disclaimer, the term of this patent is extended or adjusted under 35 U.S.C. 154(b) by 0 days.

(21) Appl. No.: 10/265,386

(22) Filed: Oct. 7, 2002

(65) Prior Publication Data

US 2003/0083201 A1 May 1, 2003

(30) Foreign Application Priority Data

Oct. 18, 2001 (JP) ........................................ 2001-320230

(51) Int. Cl.$^7$ .......................... A01N 37/00; A01N 43/60
(52) U.S. Cl. .......................... 504/136; 504/171; 504/235
(58) Field of Search ................................ 504/136, 171, 504/235; 424/405

(56) References Cited

U.S. PATENT DOCUMENTS 4,629,493 A 12/1986 Ura et al.
6,187,715 B1 * 2/2001 Narayanan et al. ......... 504/118

FOREIGN PATENT DOCUMENTS

EP 0 103 171 A1 3/1984
EP 0103171 * 3/1986

* cited by examiner

*Primary Examiner*—Alton Pryor
(74) *Attorney, Agent, or Firm*—Oliff & Berridge, PLC

(57) ABSTRACT

There is provided a novel pesticidal emulsifiable concentrate composition that contains a phenoxypropionate herbicide (e.g., quizalofop-p-ethyl), a polar solvent (e.g., N-methyl-2-pyrrolidone), non-polar solvent (e.g., aromatic or aliphatic hydrocarbon) and a surfactant (e.g., polyoxyethylene castor oil ether, polyoxyethylene styryl phenyl ether), and that is improved in low-temperature stability and emulsion stability.

7 Claims, No Drawings

PESTICIDAL EMULSIFIABLE CONCENTRATE COMPOSITION

BACKGROUND OF THE INVENTION

1. Field of the Invention

The present invention relates to a pesticidal emulsifiable concentrate composition that contains a phenoxypropionate herbicide, a polar solvent, a non-polar solvent and a surfactant, and that is improved in low-temperature stability and emulsion stability.

2. Description of the Related Art

Phenoxypropionate herbicides are herbicides effective for controlling grass weeds. And, emulsifiable concentrates are solutions composed of pesticidal active ingredients, organic solvents and surfactants, and applied generally after diluting those with water. When an emulsifiable concentrate has insufficient low-temperature stability or emulsion stability, it causes separation of crystals, or gives forth sediments or suspended matter in an emulsion obtained therefrom, thereby it is difficult to obtain a practical emulsifiable concentrate.

SUMMARY OF THE INVENTION

The present inventor conducted intensive studies and discovered the fact that a composition comprising a phenoxypropionate herbicide as an active ingredient is remarkably improved in low-temperature stability by comprising a polar solvent therein. This makes it possible to include phenoxypropionate herbicides in the composition in a high concentration. Therefore, costs in transportation and preservation can be reduced and labor of user can be eliminated or reduced. Also, the present inventor discovered the fact that an emulsion from a pesticidal emulsifiable concentrate composition is further improved in emulsion stability by mixing one or more specific surfactant selected from polyoxyethylene castor oil ether and polyoxyethylene styryl phenyl ether to the composition.

That is, the present invention relates to pesticidal emulsifiable concentrate compositions (1) to (11) as follows.

(1) A pesticidal emulsifiable concentrate composition comprising a phenoxypropionate herbicide, a polar solvent, a non-polar solvent and a surfactant.

(2) The pesticidal emulsifiable concentrate composition as set forth in the item (1), wherein the polar solvent is one or more selected from lactam and lactone.

(3) The pesticidal emulsifiable concentrate composition as set forth in the item (1), wherein the polar solvent is one or more selected from five-membered lactam and five-membered lactone.

(4) The pesticidal emulsifiable concentrate composition as set forth in the item (1), wherein the polar solvent is one or more selected from N-alkyl pyrrolidone, dimethyl imidazolidinone and y-butyrolactone.

(5) The pesticidal emulsifiable concentrate composition as set forth in the item (1), wherein the polar solvent is N-methyl-2-pyrrolidone.

(6) The pesticidal emulsifiable concentrate composition as set forth in the items (1) to (5), wherein a content of the polar solvent is 5 to 35% by weight on the basis of the pesticidal emulsifiable concentrate composition.

(7) The pesticidal emulsifiable concentrate composition as set forth in the items (1) to (6), wherein the surfactant is one or more selected from polyoxyethylene castor oil ether and polyoxyethylene styryl phenyl ether.

(8) The pesticidal emulsifiable concentrate composition as set forth in the items (1) to (7), wherein a content of the surfactant is 5 to 50% by weight on the basis of the pesticidal emulsifiable concentrate composition.

(9) The pesticidal emulsifiable concentrate composition as set forth in the items (1) to (8), wherein the phenoxypropionate herbicide is one or more selected from quizalofop-p-ethyl, quizalofop-p-teflyl and propaquizalofop.

(10) The pesticidal emulsifiable concentrate composition as set forth in the item (9), wherein the phenoxypropionate herbicide is quizalofop-p-ethyl.

(11) The pesticidal emulsifiable concentrate composition as set forth in the items (1) to (10), wherein a content of the phenoxypropionate herbicide is 16% by weight or more on the basis of the pesticidal emulsifiable concentrate composition.

DESCRIPTION OF THE PREFERRED EMBODIMENTS

In the present invention, it is necessary to use the polar solvent in an amount of 5% by weight or more in order to improve fully low-temperature stability of the pesticidal emulsifiable concentrate composition. However, if the content of the polar solvent is too much, crystals may be separated out from an emulsion obtained from the emulsifiable concentrate composition. From the standpoint of the prevention of crystal separation, the content of the polar solvent is preferably 35% by weight or less, and more preferably 25% by weight or less. Therefore, the content of the polar solvent is preferably 5 to 35% by weight, and more preferably 5 to 25% by weight.

The polar solvent is not specifically limited, but preferably lactam and lactone. The lactam includes, for example β-propiolactam, γ-butyrolactam, γ-valerolactam, dimethyl imidazolidine, N-alkyl-2-pyrrolidone, δ-valerolactam and ε-caprolactam. The lactone includes, for example β-propiolactone, γ-butyrolactone, γ-valerolactone, γ-caprolactone, γ-caprylolactone, γ-laurolactone, γ-palmitolactone, γ-stearolactone, δ-valerolactone and δ-caprolactone. Preferably, the lactam and lactone are five-membered lactam and five-membered lactone, and more preferably, N-alkyl pyrrolidone, dimethyl imidazolidinone and γ-butyrolactone. N-alkyl pyrrolidone includes, for example N-methyl-2-pyrrolidone, N-octyl-2-pyrrolidone and N-dodecyl-2-pyrrolidone, and particularly N-methyl-2-pyrrolidone is most preferable. In the meantime, the polar solvent may be used alone or in a combination of plural polar solvents.

The non-polar solvent used in the present invention is not specifically limited, and includes, for example aromatic hydrocarbons, such as xylene, alkyl ($C_8$ or $C_{10}$, etc.) benzene, phenylxylyl ethane and alkyl ($C_1$ or $C_3$, etc.) naphthalene, aliphatic hydrocarbons, such as machine oil, normal paraffin, isoparaffin and naphthene, mixtures of aromatic hydrocarbons and aliphatic hydrocarbons, such as kerosine, fat and oil, such as soybean oil, linseed oil, rapeseed oil, coconut oil, cottonseed oil and castor oil, and the like. The non-polar solvent may be also used alone or in a combination of plural non-polar solvents.

The pesticidal active ingredient used in the present invention is not specifically limited as long as it is phenoxypropionate herbicides, and includes, for example Clodinafop-propargyl (common name), Cyhalofop-butyl (common name), Diclofop-methyl (common name), Difenopenten-methyl (common name), Fenoxaprop-ethyl (common name), Fluazifop-butyl (common name), Haloxyfop (common name), Haloxyfop-methyl (common name), Isoxapyrifop (common name), Propaquizafop (common name), Quizalofop-ethyl (common name), Quizalofop-tefuryl (common name) and Fenthiaprop-ethyl (common name). Among the above-mentioned phonoxypropionate herbicides, Quizalofop-ethyl, Quizalofop-tefuryl and Propaquizafop are preferable, Quizalofop-p-ethyl, Quizalofop-p-tefuryl and Propaquizalofop are more preferable, and Quizalofop-p-ethyl is most preferable. The content of the phenoxypropionate herbicide is specifically limited, but it is desirable to contain the phenoxypropionate herbicide in a high concentration, preferably 16% by weight or more from the standpoint of elimination or reduction of labor. However, as low-temperature stability is deteriorated if the content thereof is too much, the content thereof is preferably 16 to 30% by weight. In addition, the herbicide may be used alone or in a combination of plural herbicides.

The surfactant used in the present invention is not specifically limited, and includes, for example the following surfactants (A), (B), (C), (D) and (E). These surfactants may be used alone or in a combination of plural surfactants. When the combination is used, the mixing ratio of each surfactant can be arbitrarily selected. Also, the content of the surfactant is not specifically limited, and is preferably 5 to 50% by weight.

(A) Non-Ionic Surfactants (A-1) Polyethylene glycol surfactants include, for example polyoxyethylene alkyl ($C_{12-18}$) ether, an adduct of ethylene oxide with alkylnaphthol, polyoxyethylene (mono- or di-) alkyl ($C_{8-12}$) phenyl ether, a condensate of formaldehyde with polyoxyethylene (mono- or di-) alkyl ($C_{8-12}$) phenyl ether, polyoxyethylene (mono-, di- or tri-) phenyl phenyl ether, polyoxyethylene (mono-, di- or tri-) benzyl phenyl ether, polyoxypropylene (mono-, di- or tri-) benzyl phenyl ether, polyoxyethylene (mono-, di- or tri-) styryl phenyl ether, polyoxypropylene (mono-, di- or tri-) styryl phenyl ether, a polymer of polyoxyethylene (mono-, di- or tri-) styryl phenyl ether, polyoxyethylene polyoxypropylene block polymer, alkyl ($C_{12-18}$) polyoxyethylene polyoxypropylene block polymer ether, alkyl ($C_{8-12}$) phenyl polyoxyethylene polyoxypropylene block polymer ether, polyoxyethylene bisphenyl ether, an ester of polyoxyethylene rein acid, a monoester of polyoxyethylene fatty acid ($C_{12-18}$), a diester of polyoxyethylene fatty acid ($C_{12-18}$), an ester of polyoxyethylene sorbitan fatty acid ($C_{12-18}$), glycerol fatty ester ethyleneoxide adduct, polyoxyethylene castor oil ether, hardened castor oil ethyleneoxide adduct, an alkyl ($C_{12-18}$) amine ethyleneoxide adduct and fatty acid ($C_{12-18}$) amide ethyleneoxide adduct;

(A-2) Polyhydric alcohol surfactants include, for example glycerol fatty ester, polyglycerine fatty ester, pentaerythritol fatty ester, sorbitol fatty acid ($C_{12-18}$) ester, sorbitan fatty acid ($C_{12-18}$) ester, sucrose fatty ester, polyhydric alcohol alkyl ether and fatty acid alkanolamide.

(A-3) Acetylene surfactants include, for example acetylene glycol, acetylene alcohol, an adduct of ethyleneoxide with acetylene glycol and an adduct of ethyleneoxide with acetylene alcohol.

(A-4) Other surfactants include, for example alkyl glycoside.

(B) Anionic Surfactants (B-1) Carboxylic acid surfactants include, for example carboxylic acids, such as polyacrylic acid, polymethacrylic acid, polymaleic acid, a copolymer of maleic acid with olefin (such as isobutylene or diisobutylene), a copolymer of acrylic acid with itaconic acid, a copolymer of methacrylic acid with itaconic acid, a copolymer of maleic acid with styrene, a copolymer of acrylic acid with methacrylic acid, a copolymer of acrylic acid with methyl acrylate, a copolymer of acrylic acid with vinyl acetate, a copolymer of acrylic acid with maleic acid, N-methyl-fatty acid ($C_{12-18}$) sarcosinate, resin acid and fatty acids ($C_{12-18}$), and salts of these carboxylic acids.

(B-2) Sulfate surfactants include, for example sulfate esters, such as alkyl ($C_{12-18}$) sulfate ester, polyoxyethylene alkyl ($C_{12-18}$) ether sulfate ester, polyoxyethylene (mono- or di-) alkyl ($C_{8-12}$) phenyl ether sulfate ester, a sulfate ester of polyoxyethylene (mono- or di-) alkyl ($C_{8-12}$) phenyl ether polymer, polyoxyethylene (mono-, di- or tri-) phenyl phenyl ether sulfate ester, polyoxyethylene (mono-, di- or tri-) benzyl phenyl ether sulfate ester, polyoxyethylene (mono-, di- or tri-) styryl phenyl ether sulfate ester, a sulfate ester of polyoxyethylene (mono-, di- or tri-) styryl phenyl ether polymer, a sulfate ester of polyoxyethylene polyoxypropylene block polymer, sulfated oil, sulfated fatty ester, sulfated fatty acid and sulfated olefin, and salts of those sulfate esters.

(B-3) Sulfonic acid surfactants include, for example sulfonic acids, such as paraffin ($C_{12-22}$) sulfonic acid, alkyl ($C_{8-12}$) benzene sulfonic acid, a condensate of alkyl ($C_{8-12}$) benzene sulfonic acid with formaldehyde, a condensate of cresol sulfonic acid with formaldehyde, α-olefin ($C_{14-16}$) sulfonic acid, dialkyl ($C_{8-12}$) sulfosuccinic acid, lignosulfonic acid, polyoxyethylene (mono- or di-) alkyl ($C_{8-12}$) phenyl ether sulfonic acid, polyoxyethylene alkyl ($C_{12-18}$) ether sulfosuccinic acid half ester, naphthalene sulfonic acid, (mono- or di-) alkyl ($C_{1-6}$) naphthalene sulfonic acid, a condensate of naphthalene sulfonic acid with formaldehyde, a condensate of (mono- or di-) alkyl ($C_{1-6}$) naphthalene sulfonic acid with formaldehyde, a condensate of creosote oil sulfonic acid with formaldehyde, alkyl ($C_{8-12}$) diphenylether disulfonic acid, Igepon T (trade name), polystyrene sulfonic acid and a copolymer of styrene sulfonic acid with methacrylic acid, and salts of those sulfonic acids.

(B-4) Phosphate surfactants include, for example phosphate esters, such as alkyl ($C_{8-12}$) phosphate ester, polyoxyethylene alkyl ($C_{12-18}$) ether phosphate ester, polyoxyethylene (mono- or di-) alkyl ($C_{8-12}$) phenyl ether phosphate ester, a phosphate ester of polyoxyethylene (mono-, di- or tri-) alkyl ($C_{8-12}$) phenyl ether polymer, polyoxyethylene (mono-, di- or tri-) phenyl phenyl ether phosphate ester, polyoxyethylene (mono-, di- or tri-) benzyl phenyl ether phosphate ester, polyoxyethylene (mono-, di- or tri-) styryl phenyl ether phosphate ester, a phosphate ester of polyoxyethylene (mono-, di- or tri-) styryl phenyl ether polymer, a phosphate ester of polyoxyethylene polyoxypropylene block polymer, phosphatidyl choline, phosphatidyl ethanol imine and a condensed phosphoric acid (e.g., tripolyphosphoric acid or the like), and salts of these phosphate esters.

The salts in the above-mentioned (B-1) to (B-4) include, for example salts of alkali metals (lithium, sodium or potassium), alkaline earth metals (calcium or magnesium), ammonium and several amines (e.g., alkyl amine, cycloalkyl amine or alkanol amine).

(C) Cationic Surfactants

Cationic surfactants include, for example alkyl amine salts and alkyl quaternary ammonium salts.

(D) Amphoteric Surfactants

Amphoteric surfactants include, for example betaine surfactants and amino acid surfactants.

(E) Other surfactants

Other surfactants include, for example silicone surfactants and fluorochemical surfactants.

Among the above-mentioned surfactants, polyoxyethylene castor oil ether and polyoxyethylene styryl phenyl ether are preferable.

In addition, the above-mentioned surfactants can be used as an adjuvant in order to improve the herbicidal effect of the pesticidal emulsifiable concentrate composition of the present invention. Particularly, non-ionic surfactants are preferable, and polyoxyethylene alkyl ether is more preferable. Further, other adjuvants include, for example vegetable oil and mineral oil. These adjuvants may be added to the pesticidal emulsifiable concentrate composition in advance, or mixed to an emulsion obtained from the composition.

The pesticidal emulsifiable concentrate composition of the present invention, for example, can be prepared as follows. The composition can be prepared by dissolving a phonoxypropionate herbicide that is an active ingredient, and a surfactant into a polar solvent and a non-polar solvent.

As mentioned above, the present invention provides pesticidal emulsifiable concentrate compositions that is improved in low-temperature stability and emulsion stability by adding a polar solvent, non-polar solvent and a surfactant to the compositions containing a phenoxypropionate herbicide as an active ingredient.

EXAMPLES

Examples of the pesticidal emulsifiable concentrate compositions of the present invention and comparative examples of pesticidal emulsifiable concentrate compositions for comparing therewith will hereinafter be described. In the examples and comparative examples, "parts" means parts by weight. The present invention is not limited to these examples.

Example 1

A pesticidal emulsifiable concentrate composition was prepared by adding 30 parts of N-methyl-2-pyrrolidone, 40 parts of Solvesso 200 (trade name, prepared by Exxon Mobile Corporation), 5 parts of a mixture (Solupol 3005XL (trade name), prepared by Toho Chemical Industry Co., Ltd.) of polyoxyethylene styryl phenyl ether with dodecyl benzene sulfonate and 5 parts of a mixture (Solupol 3005XH (trade name), prepared by Toho Chemical Industry Co., Ltd.) of polyoxyethylene styryl phenyl ether with dodecyl benzene sulfonate to 20 parts of quizalofop-p-ethyl, and mixing the resulting mixture.

Example 2

A pesticidal emulsifiable concentrate composition was prepared similarly to Example 1 except that 30 parts of dimethyl imidazolidinone was used instead of N-methyl-2-pyrrolidone.

Example 3

A pesticidal emulsifiable concentrate composition was prepared similarly to Example 1 except that 30 parts of γ-butyrolactone was used instead of N-methyl-2-pyrrolidone.

Example 4

A pesticidal emulsifiable concentrate composition was prepared similarly to Example 1 except that 30 parts of cyclohexanone was used instead of N-methyl-2-pyrrolidone.

Example 5

A pesticidal emulsifiable concentrate composition was prepared by adding 15 parts of N-methyl-2-pyrrolidone, 55 parts of Solvesso 200 (trade name, prepared by Exxon Mobile Corporation), 5 parts of a mixture (Solupol 3005XL (trade name), prepared by Toho Chemical Industry Co., Ltd.) of polyoxyethylene styryl phenyl ether with dodecyl benzene sulfonate and 5 parts of a mixture (Solupol 3005XH (trade name), prepared by Toho Chemical Industry Co., Ltd.) of polyoxyethylene styryl phenyl ether with dodecyl benzene sulfonate to 20 parts of quizalofop-p-ethyl, and mixing the resulting mixture.

Example 6

A pesticidal emulsifiable concentrate composition was prepared by adding 5 parts of N-methyl-2-pyrrolidone, 65 parts of Solvesso 200 (trade name, prepared by Exxon Mobile Corporation) and 10 parts of a mixture (Solupol 355F (trade name), prepared by Toho Chemical Industry Co., Ltd.) of polyoxyethylene styryl phenyl ether with dodecyl benzene sulfonate to 20 parts of quizalofop-p-ethyl, and mixing the resulting mixture.

Comparative Example 1

A pesticidal emulsifiable concentrate composition was prepared by adding 70 parts of Solvesso 200 (trade name, prepared by Exxon Mobile Corporation) and 10 parts of a mixture (Solupol 355F (trade name), prepared by Toho Chemical Industry Co., Ltd.) of polyoxyethylene styryl phenyl ether with dodecyl benzene sulfonate to 20 parts of quizalofop-p-ethyl, and mixing the resulting mixture.

Test Example 1

10 ml of each of pesticidal emulsifiable concentrate compositions prepared in Examples 1–6 and Comparative Example 1 was placed in a transparent vial, and the vial was sealed and kept at −5° C. or −15° C. for 48 hours, and thereafter it was observed on whether or not crystals were separated out. The vials in which crystals were separated out were further kept at 10° C. for 7 days, observed on re-solubility and judged on the basis of the following criteria. The results are indicated in Table 1. The criteria of crystal separation and re-solubility ◯: No crystal was separated out.

Δ: After crystals were separated out, they were resolved at 10° C.

X: After crystals were separated out, they were not resolved at 10° C.

TABLE 1

| | Low-temperature stability | | | |
| --- | --- | --- | --- | --- |
| | | | Low-temperature Stability | |
| | Polar Solvent | (% by weight) | −5° C. | −15° C. |
| Example 1 | N-methyl-2-pyrrolidone | 30 | ◯ | ◯ |
| Example 2 | Dimethyl imidazolidinone | 30 | ◯ | Δ |
| Example 3 | γ-Butyrolactone | 30 | ◯ | Δ |
| Example 4 | Cyclohexanone | 30 | Δ | Δ |
| Example 5 | N-methyl-2-pyrrolidone | 15 | ◯ | Δ |
| Example 6 | N-methyl-2-pyrrolidone | 5 | Δ | Δ |
| Comparative Example 1 | — | — | X | X |

Example 7

A pesticidal emulsifiable concentrate composition was prepared by adding 25 parts of N-methyl-2-pyrrolidone, 45 parts of Solvesso 200 (trade name, prepared by Exxon Mobile Corporation), 5 parts of a mixture (Solupol 3005XL (trade name), prepared by Toho Chemical Industry Co., Ltd.) of polyoxyethylene styryl phenyl ether with dodecyl benzene sulfonate and 5 parts of a mixture (Solupol 3005XH (trade name), prepared by Toho Chemical Industry Co., Ltd.) of polyoxyethylene styryl phenyl ether with dodecyl benzene sulfonate to 20 parts of quizalofop-p-ethyl, and mixing the resulting mixture.

Test Example 2

100 ml of hard water having hardness of 19.2 was placed in 100 ml measuring cylinder, 1 ml of each of pesticidal emulsifiable concentrate compositions prepared in Examples 1 and 7 was added thereto, and the cylinder was turned upside down to emulsify homogeneously the liquid therein. The resulting emulsion was left at 15° C. for 24 hours, then was filtered with suction using a filer paper having a sieve opening of 3 µm, and thereafter it was observed on whether or not crystals were present.

TABLE 2

Evaluation on crystals in emulsion

| | Polar Solvent | (% by weight) | Whether crystals are present or absent |
|---|---|---|---|
| Example 1 | N-methyl-2-pyrrolidone | 30 | Present (extremely slight amount) |
| Example 7 | N-methyl-2-pyrrolidone | 25 | Absent |

Example 8

A pesticidal emulsifiable concentrate composition was prepared by adding 15 parts of N-methyl-2-pyrrolidone, 55 parts of Solvesso 200 (trade name, prepared by Exxon Mobile Corporation), 6 parts of polyoxyethylene styryl phenyl ether (Solupol T-20 (trade name), prepared by Toho Chemical Industry Co., Ltd.) and 4 parts of dodecyl benzene sulfonate (Solupol EX-15 (trade name), prepared by Toho Chemical Industry Co., Ltd.) to 20 parts of quizalofop-p-ethyl, and mixing the resulting mixture.

Example 9

A pesticidal emulsifiable concentrate composition was prepared by adding 15 parts of N-methyl-2-pyrrolidone, 55 parts of Solvesso 200 (trade name, prepared by Exxon Mobile Corporation), 4 parts of polyoxyethylene castor oil ether (Solupol CA-42 (trade name), prepared by Toho Chemical Industry Co., Ltd.) and 6 parts of dodecyl benzene sulfonate (Solupol EX-15 (trade name), prepared by Toho Chemical Industry Co., Ltd.) to 20 parts of quizalofop-p-ethyl, and mixing the resulting mixture.

Example 10

A pesticidal emulsifiable concentrate composition was prepared similarly to Example 8 except that 6 parts of polyoxyethylene styryl phenyl ether polymer (Solupol F-18 (trade name), prepared by Toho Chemical Industry Co., Ltd.) was used instead of polyoxyethylene styryl phenyl ether.

Example 11

A pesticidal emulsifiable concentrate composition was prepared similarly to Example 8 except that 6 parts of polyoxyethylene nonyl phenyl ether (Solupol N-10 (trade name), prepared by Toho Chemical Industry Co., Ltd.) was used instead of polyoxyethylene styryl phenyl ether.

Example 12

A pesticidal emulsifiable concentrate composition was prepared similarly to Example 8 except that 6 parts of polyoxyethylene alkyl ether (Noigen ET-135 (trade name), prepared by Dai-ichi Kogyo Seiyaku Co., Ltd.) was used instead of polyoxyethylene styryl phenyl ether.

Example 13

A pesticidal emulsifiable concentrate composition was prepared similarly to Example 8 except that 6 parts of polyoxyethylene sorbitan ester (Sorubon T-60 (trade name), prepared by Toho Chemical Industry Co., Ltd.) was used instead of polyoxyethylene styryl phenyl ether.

Test Example 3

Emulsions prepared by emulsifying pesticidal emulsifiable concentrate compositions similarly to Test Example 2 were left at 30° C., and sediments therein were observed after 1 hour and 24 hours. The results are indicated in Table 3.

TABLE 3

Emulsion stability of emulsion

| | Amount of Sediments (ml) | |
|---|---|---|
| | After 1 hour | After 24 hours |
| Example 8 | 0 | 0 |
| Example 9 | 0 | less than 0.1 |
| Example 10 | 0.1 | — |
| Example 11 | 0.5 | — |
| Example 12 | 0.3 | — |
| Example 13 | 0.5 | — |

What is claimed is:

1. A pesticidal emulsifiable concentrate composition consisting of a phenoxypropionate herbicide, a polar solvent, a non-polar solvent and a surfactant, wherein said polar solvent is N-methyl-2-pyrrolidone.

2. The pesticidal emulsifiable concentrate composition according to claim 1, wherein a content of the polar solvent is 5 to 35% by weight on the basis of the pesticidal emulsifiable concentrate composition.

3. The pesticidal emulsifiable concentrate composition according to claim 1, wherein the surfactant is one or more selected from polyoxyethylene castor oil ether and polyoxyethylene styryl phenyl ether.

4. The pesticidal emulsifiable concentrate composition according to claim 1, wherein a content of the surfactant is 5 to 50% by weight on the basis of the pesticidal emulsifiable concentrate composition.

5. The pesticidal emulsifiable concentrate composition according to claim 1, wherein the phenoxypropionate herbicide is one or more selected from quizalofop-p-ethyl, quizalofop-p-teflyl and propaquizalofop.

6. The pesticidal emulsifiable concentrate composition according to claim 5, wherein the phenoxypropionate herbicide is quizalofop-p-ethyl.

7. The pesticidal emulsifiable concentrate composition according to claim 1, wherein a content of the phenoxypropionate herbicide is 16% by weight or more on the basis of the pesticidal emulsifiable concentrate composition.

* * * * *